(12) United States Patent
Hu et al.

(10) Patent No.: US 11,703,495 B2
(45) Date of Patent: Jul. 18, 2023

(54) METHOD FOR IDENTIFYING AND ANALYZING DISSOLVED ORGANIC NITROGEN OF DIFFERENT SOURCES IN WASTEWATER AND APPLICATION OF THE METHOD

(71) Applicant: Nanjing University, Nanjing (CN)

(72) Inventors: Haidong Hu, Nanjing (CN); Kewei Liao, Nanjing (CN); Hongqiang Ren, Nanjing (CN)

(73) Assignee: NANJING UNIVERSITY, Nanjing (CN)

( * ) Notice: Subject to any disclaimer, the term of this patent is extended or adjusted under 35 U.S.C. 154(b) by 97 days.

(21) Appl. No.: 17/483,777

(22) Filed: Sep. 23, 2021

(65) Prior Publication Data
US 2022/0042963 A1 Feb. 10, 2022

(30) Foreign Application Priority Data
Jun. 22, 2021 (CN) .......................... 202110691892.4

(51) Int. Cl.
  *G01N 33/18* (2006.01)
  *G01N 30/86* (2006.01)
  *G01N 30/72* (2006.01)

(52) U.S. Cl.
  CPC ..... *G01N 33/1826* (2013.01); *G01N 30/7233* (2013.01); *G01N 30/8686* (2013.01)

(58) Field of Classification Search
  CPC ........... G01N 33/1826; G01N 30/7233; G01N 30/8686; G01N 2030/8872; G01N 30/02; G01N 30/06; G01N 30/72; G01N 30/8679; G01N 2030/062; Y02A 20/20
  See application file for complete search history.

(56) References Cited

FOREIGN PATENT DOCUMENTS
CN  106771043 A  *  5/2017  ............... C02F 9/00

* cited by examiner

*Primary Examiner* — Jennifer Wecker
*Assistant Examiner* — Michael Paul Shimek
(74) *Attorney, Agent, or Firm* — Matthias Scholl P.C.; Matthias Scholl

(57) ABSTRACT

A method for identifying and analyzing dissolved organic nitrogen of different sources in wastewater includes extracting DON in wastewater to obtain a DON extract, detecting mass spectrum peaks in the DON extract, pre-processing the spectral data of the wastewater sample; constructing a network relationship of the substance reaction in the wastewater sample; screening the substance reaction relationship of DON; and determining different sources of DON.

10 Claims, 4 Drawing Sheets

Effluent from a biological section of Plant A

METHOD FOR IDENTIFYING AND ANALYZING DISSOLVED ORGANIC NITROGEN OF DIFFERENT SOURCES IN WASTEWATER AND APPLICATION OF THE METHOD

CROSS-REFERENCE TO RELATED APPLICATIONS

Pursuant to 35 U.S.C. § 119 and the Paris Convention Treaty, this application claims foreign priority to Chinese Patent Application No. 202110691892.4 filed Jun. 22, 2021, the contents of which, including any intervening amendments thereto, are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, Cambridge, Mass. 02142.

BACKGROUND

The disclosure relates to the field of wastewater treatment, and more particularly to a method for identifying and analyzing dissolved organic nitrogen of different sources in wastewater and application of the method.

Dissolved organic nitrogen (DON) is an important component of dissolved total nitrogen in municipal wastewater treatment plants. DON in wastewater can operate as a precursor of disinfection by-products, which produce carcinogenic disinfection by-products during the disinfection stage. In addition, the DON in the effluent of a wastewater plant can stimulate the growth of algae and cause eutrophication. In urban wastewater treatment plants, DON in wastewater can be divided into exogenous DON and endogenous DON according to their sources. Exogenous DON is from influent water of a wastewater treatment plant, including DON that has not been completely degraded in the wastewater treatment process, and DON that is non-degradable or difficult to degrade in the influent water. Endogenous DON is from wastewater treatment process, including microorganism DON, microbial conversion products of exogenous DON, DON by-products of wastewater treatment process. Existing studies have shown that exogenous DON and endogenous DON have significant differences in the main molecular composition, conversion behavior, environmental impact, and regulatory factors, etc. Therefore, it is necessary to distinguish exogenous DON from endogenous DON when evaluating the operation effect and formulating operation control strategies for wastewater treatment plants.

In the process of urban wastewater treatment, exogenous DON and endogenous DON can co-exist in the wastewater, which makes it difficult to separate exogenous DON from endogenous DON using conventional analytical techniques. The identification and analysis of different sources of DON mainly involves two levels: the macroscopic concentration level and the molecular composition level. At the macroscopic concentration level, the existing methods adopt the mathematical model prediction or simulated wastewater experiments to determine the concentration of endogenous DON in wastewater, to solve the quantitative problem of endogenous DON in the mixed system, and further realize the quantification of exogenous DON through a subtraction method. At the molecular composition level, the existing methods resolve the qualitative problem of exogenous DON and endogenous DON by analyzing the typical characteristic components of different sources of DON. Although a breakthrough has been achieved in the identification and analysis of different sources of DON, it is still a huge challenge to distinguish different sources of DON at both the macroscopic concentration level and the molecular composition level.

SUMMARY

One object of the disclosure is to solve the problem of distinguishing the exogenous DON from the endogenous DON at both the macroscopic concentration level and the molecular composition level in the wastewater, and improve the dependence of the existing methods on equipment and parameter conditions, and thus provide a method for identifying and analyzing dissolved organic nitrogen of different sources in wastewater.

The disclosure provides a method for identifying and analyzing dissolved organic nitrogen of different sources in wastewater, which is a simultaneous qualitative and quantitative method for exogenous DON and endogenous DON in wastewater samples established by liquid chromatography-high resolution mass spectrometry technology and reaction omics analysis technology. The method comprises the following steps:

(a) extracting DON in wastewater: separating dissolved organic nitrogen (DON) from interferents of a wastewater sample through operations comprising pretreatment of the wastewater sample, column activation, sample loading, leaching, and elution using solid phase extraction cartridges (SPE cartridges), concentrating and enriching DON in the wastewater sample, to obtain a DON extract;

(b) detecting mass spectrum peaks in the DON extract: performing full scan analysis and detection of the DON extract using a liquid chromatography-high resolution mass spectrometer (LC-HRMS), to obtain a detection spectrum of DON in the wastewater sample;

(c) pre-processing the spectral data of the wastewater sample: performing subtraction of background signal values, elimination of interference peaks, and elimination of noise signals from the detection spectrum of DON in the wastewater sample, to obtain preprocessed spectral data of the wastewater sample;

(d) constructing a network relationship of the substance reaction in the wastewater: performing extraction of peaks of the spectral data of the wastewater sample, hierarchical clustering of a retention time, and peak de-redundancy of the wastewater sample using a reaction omics analysis technology, to simplify the spectral data of the wastewater sample; establishing a global reaction quality difference relationship, screening independent mass spectrum peaks, and constructing a high-frequency mass difference matrix of a substance reaction in the wastewater sample; combining the high-frequency mass difference matrix and a substance reaction database to generate a network relationship diagram of the substance reaction in the wastewater sample;

(e) screening the substance reaction relationship of DON: matching the mass spectrum peaks in the network relationship diagram with a mass spectral database to obtain a molecular formula of the substance corresponding to the mass spectrum peaks, screening a high-frequency mass difference relationship associated with DON in the network relationship diagram to obtain a substance reaction relationship of DON; and (f) determining different sources of DON: calculating a reaction relationship connectivity degree and a reaction distance of each DON molecule in the substance reaction relationship of DON, and dividing exogenous DON and endogenous DON according to the reaction relationship connectivity degree and the reaction distance.

In a class of this embodiment, the wastewater sample is selected from a single treatment unit in an urban wastewater treatment plant, a collection of wastewater samples from a plurality of treatment units in an urban wastewater treatment plant, a collection of wastewater samples from an entire process of an urban wastewater treatment plant, and effluent samples from an urban wastewater treatment plant; exogenous DON is the DON that has not been completely degraded in the wastewater treatment process, and the DON that is non-degradable or difficult to biodegrade in the influent; endogenous DON is a microbial DON, a microbial conversion product of exogenous DON, and a DON by-product of the wastewater treatment process.

In a class of this embodiment, in a), the SPE cartridges are commercial SPE cartridges using styrene-divinylbenzene copolymer as a filler; the pretreatment of the wastewater sample is to filter the wastewater sample through a 0.45 μm cellulose acetate filter membrane and acidify the wastewater sample to pH 2 using an ACS grade high-purity hydrochloric acid; the column activation is to pass 10-15 mL of LC-MS grade methanol and 20-25 mL of ultrapure water with pH 2 through the SPE cartridges; the leaching is to pass 20-25 mL of ultrapure water with pH 2 through the SPE cartridges; the elution is to blow the SPE cartridges with nitrogen to remove a liquid therein and then pass 5-15 mL of LC-MS grade methanol through the SPE cartridges; a flow rate of an eluent passing through the SPE cartridges is controlled to be 0.5-2.0 mL/min; the DON extract is filtered through a 0.22 μm organic filter membrane before being tested on a machine, and a concentration of dissolved organ carbon is 50-100 mg/L.

In a class of this embodiment, in b), the LC-HRMS operates under the following parameters: the scanning mode is a positive ion and negative ion mode; the ionization source is an electrospray ionization source, and a flow rate is 0.2-0.5 mL/min; and a range of a collected spectra is 50-1200 Da.

In a class of this embodiment, in c), the background signal values are acquired as follows: background signals are acquired through operations in a) and b) using ultrapure water as a sample to be processed; the background signals are subtracted by a peak intensity subtraction method, and mass spectrum peaks with a peak intensity≥1000 after subtraction are retained; and the spectral data of the wastewater sample are ".mzrt" data converted by a "XCMS" program package in a R language In a class of this embodiment, in d), for the reaction omics analysis technology, in the process of biochemical reaction, the substance reaction process involving in DON has corresponding reactant DON and reaction product DON, and a specific relationship between the reactant DON and the reaction product DON; under the condition that the substance reaction process is unknown, the substance reaction process involving the reactant DON, the reaction product DON, and DON in the sample is obtained according to the mass difference relationship;

the peak de-redundancy is to deduct redundant mass spectrum peaks in the spectral data of the wastewater samples;

the hierarchical clustering of the retention time is to calculate the mass difference relationship in wastewater samples using the "getpaired" function in the R language, and cluster the retention time according to the recursion formula (1), with a D value greater than 10 as the cutoff grouping threshold:

$$D = \frac{\sqrt{(RT_m - RT_j)^2} + \sqrt{(RT_n - RT_j)^2}}{2}; \quad (1)$$

where, $RT_m$ and $RT_n$ are combined clusters of retention time data; $RT_1$ is a single retention time data to be calculated, and D is the distance between $RT_1$ and the combined clusters $(RT_m, RT_n)$ of the retention time data; the high-frequency mass difference relationship is a mass difference relationship after deducting the adduct, neutral loss, isotope, and common fragments in the mass difference relationship using the "getstd" function in the R language; the high-frequency mass difference matrix is a substance reaction matrix with the mass spectrum peak as a matrix element according to the formula (2):

$$\begin{array}{c|cccc} & B_1 & B_2 & \ldots & B_n \\ P_1 & |B_1 - P_1| & |B_2 - P_1| & \ldots & |B_n - P_1| \\ P_2 & |B_1 - P_2| & |B_2 - P_2| & \ldots & |B_n - P_2| \\ \ldots & \ldots & \ldots & \ldots & \ldots \\ P_m & |B_1 - P_m| & |B_2 - P_m| & \ldots & |B_n - P_m| \end{array} \quad (2)$$

where, $\{P_1, P_2, \ldots, P_m\}$ is a mass spectrum peak, and $\{B_1, B_2, \ldots, B_n\}$ is a potential parent reactant of the mass spectrum peak;

the substance reaction database is KEGG database and HMDB database; and the network relationship diagram of the substance reaction is a topological relationship with the minimum mass difference of the substance reaction as a link, the mass spectrum peak as a node, and the correlation value≥0.6.

In a class of this embodiment, the minimum mass difference is calculated according to the following formula:

$$PMD_{Bk} = \{\min(|B_k - P_1|, |B_k - P_2|, \ldots, |B_k - P_m|)| \\ k = 1, 2, \ldots, n\} \quad (3)$$

where, $PMD_{BK}$ is the minimum mass difference of the substance reaction, $\{P_1, P_2, \ldots, P_m\}$ is a mass spectrum peak, and $\{B_1, B_2, \ldots, B_n\}$ is a potential parent reactant of the mass spectrum peak.

In a class of this embodiment, in e), the molecular formula matching rule of the substance corresponding to the mass spectrum peak is that the mass spectrum peak error is <5 ppm, the retention time error is <2 min, the relative molecular mass of the DON molecule containing an even number of nitrogen atoms is an even number, the relative molecular mass of the DON molecule containing an odd number of nitrogen atoms is an odd number, and the score for molecular formula matching is >90.

In a class of this embodiment, in f), the connectivity degree is the number of substance reactions in which each DON molecule is involved in the adjacency matrix of the substance reaction relationship;

the reaction distance is a connection distance among DON molecules in the adjacency matrix of the substance reaction relationship, that is, in the adjacency matrix $A=(a_{ij})_{N \times N}$, the connectivity degree of DON molecules is $k_i = \sum_{j=1}^{N} a_{ij}$, and the reaction distance of DON molecules is $$L = \frac{1}{\frac{1}{2}N(N-1)} \sum_{i \geq j} l_{ij},$$

where, A is an adjacency matrix, $a_{ij}$ is a relationship descriptor between DON molecule i and DON molecule j, N is the number of DON molecules, $k_i$ is the connectivity degree of DON molecule i, and $l_{ij}$ is the number of the shortest connection relationship between DON molecule i and DON molecule j, L is the average connection length of the substance reaction relationship network of DON;

the division by the reaction relationship connectivity degree and the reaction distance is to use the median of the connectivity degree in the wastewater sample as the main cut-off value and the median of the reaction distance as the secondary cut-off value, to divide DON molecules of $\{k_i \leq \mathrm{median}(k_i)\} \cap \{l_{ij} \geq \mathrm{median}(l_{ij})\}$ as exogenous DON molecules, and DON molecules of $\{k_i > \mathrm{median}(k_i)\} \cup \{l_{ij} < \mathrm{median}(l_{ij})\}$ as endogenous DON molecules, where $\mathrm{median}(k_i)$ is the median of the connectivity degree, and $\mathrm{median}(l_{ij})$ is the median of the reaction distance.

The disclosure further provides an application of the above method. The method is applied to the qualitative and quantitative determination of exogenous and endogenous dissolved organic nitrogen in wastewater, to quantify the ratio of the exogenous DON to endogenous DON.

The following advantages are associated with the method of the disclosure:

(1) The method can qualitatively and quantitatively identify and analyze DON from different sources at the macroscopic concentration and molecular composition levels, and is easy to operate.

(2) In the disclosure, based on the reaction principle and rules of DON in the wastewater sample system and combing the rapid detection and high-efficiency separation characteristics of the LC-HRMS, the effective and high-frequency substance reaction relationships are pre-screened, which greatly simplifies the calculation steps, reduces the false positive detection rate, and can ensure the high throughput and accuracy of the detection.

(3) The disclosure utilizes the reaction omics analysis technology to explore the inherent reaction relationship of DON molecules in wastewater, and performs classification of DON from different sources based on the difference in the topological structure of the substance reaction relationship of DON, which reduces the dependence of existing methods on instrument conditions, enhances the universal applicability of the method for identifying and analyzing DON from different sources, and improves the applicability of the method.

DETAILED DESCRIPTION

To further illustrate the disclosure, embodiments detailing a method for identifying and analyzing dissolved organic nitrogen of different sources in wastewater are described below. It should be noted that the following embodiments are intended to describe and not to limit the disclosure.

Example 1

Figure 1:
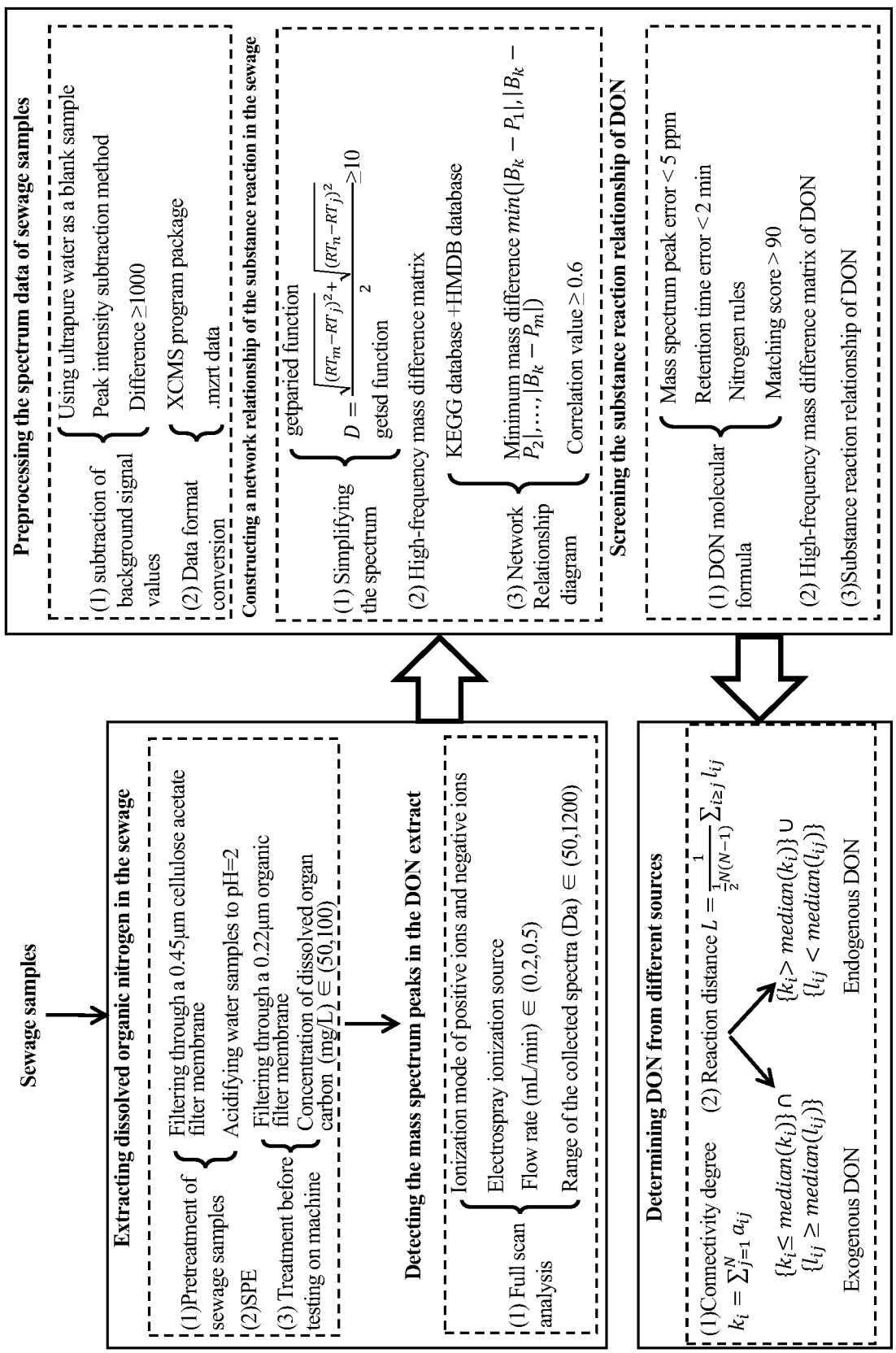
FIG. 1 is a flow block diagram for identifying and analyzing dissolved organic nitrogen of different sources in wastewater in the disclosure.

The application object of this example was an effluent from the biological section of a wastewater treatment plant A, with a daily treatment capacity of wastewater of 45,000 cubic meters per day and an oxidation ditch as the main process. The effluent of the biological section contained COD 25.59 mg/L, total nitrogen 7.31 mg/L, total phosphorus 0.40 mg/L, ammonia nitrogen 0.06 mg/L, nitrate nitrogen 2.31 mg/L, nitrite nitrogen 0.09 mg/L, DON 4.85 mg/L. The steps for identifying and analyzing exogenous DON and endogenous DON in the effluent from the biological section of Plant A were shown in FIG. 1. A method for identifying and analyzing dissolved organic nitrogen of different sources in wastewater, which was a simultaneous qualitative and quantitative method for exogenous DON and endogenous DON in wastewater samples established by liquid chromatography-high resolution mass spectrometry technology and reaction omics analysis technology, comprised the following steps:

Step 1: Extracting DON in wastewater. A commercial SPE cartridges with styrene-divinylbenzene copolymer as the filler was used to concentrate and enrich DON in the wastewater sample. Wastewater samples were firstly filtered through a 0.45 μm cellulose acetate filter membrane, and acidified with ACS grade high-purity hydrochloric acid to pH 2, then the SPE cartridges were activated using 10 mL of LC-MS grade methanol and 20 mL of ultrapure water with pH 2. Samples were loaded at a flow rate of 0.5 mL/min, then SPE cartridges were rinsed with 20 mL of pH 2 ultrapure water, and finally dried with nitrogen. After eluted with 10 mL of LC-MS grade methanol, DON extract to be detected was obtained. Before testing on the machine, the DON extract was filtered through a 0.22 μm organic filter membrane, and the concentration of the dissolved organic carbon was 100 mg/L.

Step 2: Detecting mass spectrum peaks in the DON extract. A full scan analysis and detection of the DON extract was performed using a LC-HRMS. The scanning mode of the LC-HRMS was set to ionization mode of positive ions and negative ions, the ionization source was electrospray ionization source, the flow rate was 0.2 mL/min, the range of the collected spectra was 50-1200 Da. The detection spectrum of DON in the wastewater sample was obtained after testing on the machine.

Step 3: Pre-processing the spectral data of the wastewater samples. Using ultrapure water as a sample to be treated, the operation procedure same as those for the wastewater samples were carried out to obtain background signals; the background signals were subtracted by a peak intensity subtraction method, and the mass spectrum peaks with peak intensity≥1000 after the subtraction were retained. The background subtraction, elimination of interference peaks, and elimination of noise signals were performed for the detection spectrum of wastewater samples, and then the wastewater sample spectral data were converted into ".mzrt" data by the "XCMS" program package in the R language.

Step 4: Constructing a network relationship of the substance reaction in the wastewater: performing extraction of peaks of the spectral data of the wastewater samples, hierarchical clustering of the retention time, and peak de-redundancy of the wastewater samples using a reaction omics analysis technology, to simplify the spectral data of the wastewater samples; establishing a global reaction quality difference relationship, screening independent mass spectrum peaks, and constructing a high-frequency mass difference matrix of the substance reaction in the wastewater sample; combining the high-frequency mass difference matrix and the substance reaction database to generate a network relationship diagram of the substance reaction in the wastewater. For the reaction omics analysis technology, in the process of biochemical reaction, the substance reaction process in which the DON was involved had its corresponding reactant DON and reaction product DON, and a specific relationship between the reactant DON and the reaction product DON; under the condition that the substance reaction process was unknown, the substance reaction process involving the reactant DON, the reaction product DON, and DON in the sample could be obtained according to the mass difference relationship; The peak de-redundancy was to deduct redundant mass spectrum peaks in the spectral data of the wastewater samples; The hierarchical clustering of the retention time was to calculate the mass difference relationship in wastewater samples using the "getpaired" function in the R language, and cluster the retention time according to the recursion formula $$D = \frac{\sqrt{(RT_m - RT_j)^2} + \sqrt{(RT_n - RT_j)^2}}{2},$$

with a D value greater than 10 as the cutoff grouping threshold. Where, $RT_m$ and $RT_n$ were combined clusters of retention time data; $RT_1$ was a single retention time data to be calculated, and D was the distance between $RT_1$ and the combined clusters $(RT_m, RT_n)$ of the retention time data; the high-frequency mass difference relationship was a mass difference relationship after deducting the adduct, neutral loss, isotope, and common fragments in the mass difference relationship using the "getstd" function in the R language; the high-frequency mass difference matrix was a substance reaction matrix with the mass spectrum peak as a matrix element, namely:

|   | $B_1$ | $B_2$ | ... | $B_n$ |
|---|---|---|---|---|
| $P_1$ | $|B_1 - P_1|$ | $|B_2 - P_1|$ | ... | $|B_n - P_1|$ |
| $P_2$ | $|B_1 - P_2|$ | $|B_2 - P_2|$ | ... | $|B_n - P_2|$ |
| ... | ... | ... | ... | ... |
| $P_m$ | $|B_1 - P_m|$ | $|B_2 - P_m|$ | ... | $|B_n - P_m|$ |

Where, $\{P_1, P_2, \ldots, P_m\}$ was a mass spectrum peak, and $\{B_1, B_2, \ldots, B_n\}$ was a potential parent reactant of the mass spectrum peak; the substance reaction database is KEGG database and HMDB database; the network relationship diagram of the substance reaction was a topological relationship with the minimum mass difference of the substance reaction as a link, the mass spectrum peak as a node, and the correlation value$\geq 0.6$. The minimum mass difference is calculated according to the following formula:

$PMD_{Bk} = \{min(|B_k - P_1|, |B_k - P_2|, \ldots, |B_k - P_m|)|$
$k = 1, 2, \ldots, n\};$ Step 5: Screening the substance reaction relationship of DON. According to the matching rules that the mass spectrum peak error was <5 ppm, the retention time error was <2 min, the relative molecular mass of the DON molecule containing an even number of nitrogen atoms was an even number, the relative molecular mass of the DON molecule containing an odd number of nitrogen atoms was an odd number, and the score for molecular formula matching was >90, the mass spectrum peaks in the network relationship diagram was matched with the mass spectral database to obtain the molecular formula of the substance corresponding to the mass spectrum peak, and the high-frequency mass difference relationship associated with DON in the network relationship diagram was screened, to obtain a substance reaction relationship of DON.

Step 6: Determining different sources of DON: Calculating the reaction relationship connectivity degree and a reaction distance of each DON molecule in the substance reaction relationship of DON, and dividing exogenous DON and endogenous DON according to the reaction relationship connectivity degree and the reaction distance. The connectivity degree was the number of substance reactions in which each DON molecule was involved in the adjacency matrix of the substance reaction relationship. The reaction distance was a connection distance among DON molecules in the adjacency matrix of the substance reaction relationship, that is, in the adjacency matrix $A = (a_{ij})_{N \times N}$, the connectivity degree of DON molecules was $k_i = \Sigma_{j=1}^{N} a_{ij}$, and the reaction distance of DON molecules was $$L = \frac{1}{\frac{1}{2}N(N-1)} \sum_{i \geq j} l_{ij},$$

where, A was an adjacency matrix, $a_{ij}$ was a relationship descriptor between DON molecule i and DON molecule j, N was the number of DON molecules, $k_i$ was the connectivity degree of DON molecule i, and $l_{ij}$ was the number of the shortest connection relationship between DON molecule i and DON molecule j, L was the average connection length of the substance reaction relationship network of DON. The division by the reaction relationship connectivity degree and the reaction distance was to use the median of the connectivity degree in the wastewater sample as the main cut-off value and the median of the reaction distance as the secondary cut-off value, to divide DON molecules of $\{k_i \leq median(k_i)\} \cap \{l_{ij} \geq median(l_{ij})\}$ as exogenous DON molecules, and DON molecules of $\{k_i > median(k_i)\} \cup \{l_{ij} < median(l_{ij})\}$ as endogenous DON molecules, where median($k_i$) was the median of the connectivity degree, and median($l_{ij}$) was the median of the reaction distance.

Figure 2:
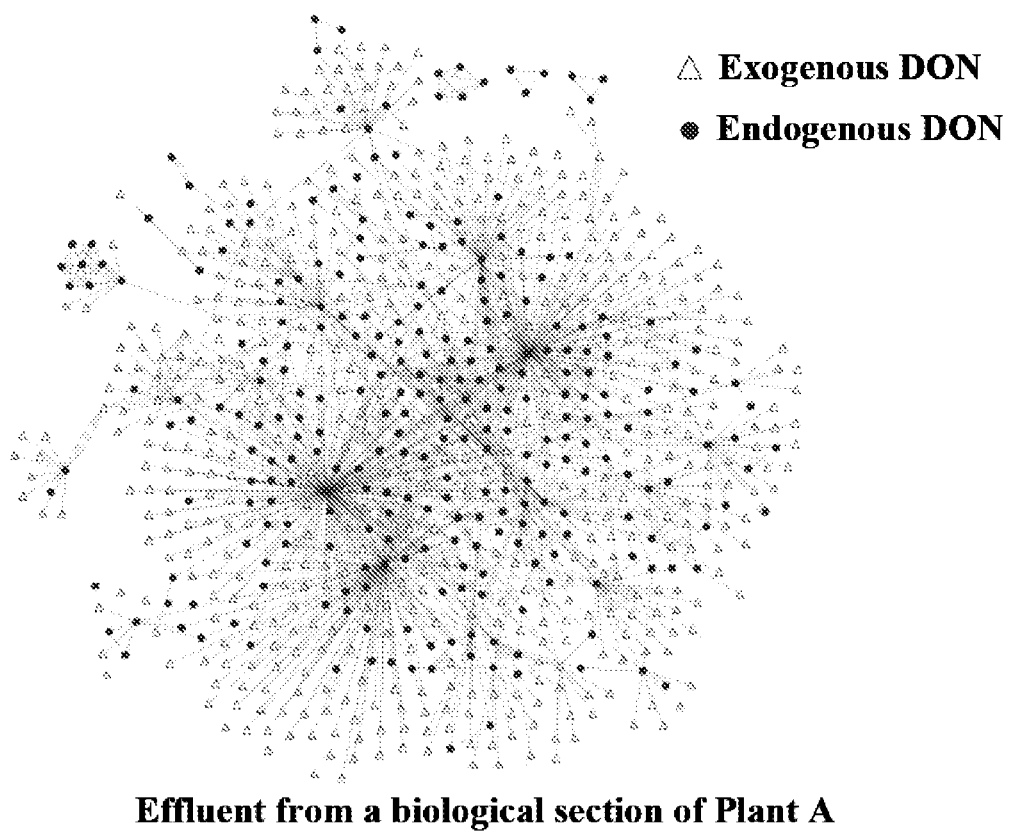
FIG. 2 is a topological structure diagram of a substance reaction of DON from different sources according to Example 1 of the disclosure.

As shown in FIG. 2, the DON molecules in the effluent from the biological section of Plant A were divided into exogenous DON molecules and endogenous DON molecules by this method, and then the mass spectrum peak intensity values of exogenous DON molecules and endogenous DON molecules were calculated respectively. Thus, it could be confirmed that, in the effluent from the biological section of Plant A with a DON concentration at 4.85 mg/L, the exogenous DON accounted for 58.3%, and endogenous DON accounted for 41.7%.

Example 2

Different from Example 1, the application object of this example was the total effluent of a wastewater treatment plant B, with a daily treatment capacity of wastewater of 150,000 cubic meters per day and main water treatment process of $A^2$/O process+secondary sedimentation tank+high-efficiency sedimentation tank+quartz sand filter. The total effluent contained COD 17.32 mg/L, total nitrogen 10.95 mg/L, total phosphorus 0.10 mg/L, ammonia nitrogen 0.33 mg/L, nitrate nitrogen 7.47 mg/L, nitrite nitrogen 0.04 mg/L, DON 3.11 mg/L. The steps for identifying and analyzing exogenous DON and endogenous DON in the total effluent from Plant B were shown in FIG. 1. A method for identifying and analyzing dissolved organic nitrogen of different sources in wastewater, which was a simultaneous qualitative and quantitative method for exogenous DON and endogenous DON in wastewater samples established by liquid chromatography-high resolution mass spectrometry technology and reaction omics analysis technology, comprised the following steps:

Step 1: Extracting DON in wastewater. A commercial SPE cartridges with styrene-divinylbenzene copolymer as the filler was used to concentrate and enrich DON in the wastewater sample. Wastewater samples were firstly filtered through a 0.45 μm cellulose acetate filter membrane, and acidified with ACS grade high-purity hydrochloric acid to pH 2, then the SPE cartridges were activated using 15 mL of LC-MS grade methanol and 25 mL of ultrapure water with pH 2. Samples were loaded at a flow rate of 2.0 mL/min, then SPE cartridges were rinsed with 25 mL of pH 2 ultrapure water, and finally dried with nitrogen. After eluted with 15 mL of LC-MS grade methanol, DON extract to be detected was obtained. Before testing on the machine, the DON extract was filtered through a 0.22 μm organic filter membrane, and the concentration of the dissolved organic carbon was 70 mg/L.

Step 2: Detecting mass spectrum peaks in the DON extract. A full scan analysis and detection of the DON extract was performed using a LC-HRMS. The scanning mode of the LC-HRMS was set to ionization mode of positive ions and negative ions, the ionization source was electrospray ionization source, the flow rate was 0.5 mL/min, the range of the collected spectra was 100-1000 Da. The detection spectrum of DON in the wastewater sample was obtained after testing on the machine.

Step 3: Pre-processing the spectral data of the wastewater samples. Using ultrapure water as a sample to be treated, the operation procedure same as those for the wastewater samples were carried out to obtain background signals; the background signals were subtracted by a peak intensity subtraction method, and the mass spectrum peaks with peak intensity≥3000 after the subtraction were retained. The background subtraction, elimination of interference peaks, and elimination of noise signals were performed for the detection spectrum of wastewater samples, and then the wastewater sample spectral data were converted into ".mzrt" data by the "XCMS" program package in the R language.

Step 4: Constructing a network relationship of the substance reaction in the wastewater: performing extraction of peaks of the spectral data of the wastewater samples, hierarchical clustering of the retention time, and peak de-redundancy of the wastewater samples using a reaction omics analysis technology, to simplify the spectral data of the wastewater samples; establishing a global reaction quality difference relationship, screening independent mass spectrum peaks, and constructing a high-frequency mass difference matrix of the substance reaction in the wastewater sample; combining the high-frequency mass difference matrix and the substance reaction database to generate a network relationship diagram of the substance reaction in the wastewater. Where, for the reaction omics analysis technology, in the process of biochemical reaction, the substance reaction process in which the DON was involved had its corresponding reactant DON and reaction product DON, and a specific relationship between the reactant DON and the reaction product DON; under the condition that the substance reaction process was unknown, the substance reaction process involving the reactant DON, the reaction product DON, and DON in the sample could be obtained according to the mass difference relationship; The peak de-redundancy was to deduct redundant mass spectrum peaks in the spectral data of the wastewater samples; The hierarchical clustering of the retention time was to calculate the mass difference relationship in wastewater samples using the "getpaired" function in the R language, and cluster the retention time according to the recursion formula $$D = \frac{\sqrt{(RT_m - RT_j)^2} + \sqrt{(RT_n - RT_j)^2}}{2},$$

with a D value greater than 20 as the cutoff grouping threshold. Where, $RT_m$ and $RT_n$ were combined clusters of retention time data; $RT_1$ was a single retention time data to be calculated, and D was the distance between $RT_1$ and the combined clusters $(RT_m, RT_n)$ of the retention time data; the high-frequency mass difference relationship was a mass difference relationship after deducting the adduct, neutral loss, isotope, and common fragments in the mass difference relationship using the "getstd" function in the R language; the high-frequency mass difference matrix was a substance reaction matrix with the mass spectrum peak as a matrix element, namely:

|     | $B_1$ | $B_2$ | ... | $B_n$ |
|-----|-------|-------|-----|-------|
| $P_1$ | $|B_1 - P_1|$ | $|B_2 - P_1|$ | ... | $|B_n - P_1|$ |
| $P_2$ | $|B_1 - P_2|$ | $|B_2 - P_2|$ | ... | $|B_n - P_2|$ |
| ... | ... | ... | ... | ... |
| $P_m$ | $|B_1 - P_m|$ | $|B_2 - P_m|$ | ... | $|B_n - P_m|$ |

Where, $\{P_1, P_2, \ldots, P_m\}$ was a mass spectrum peak, and $\{B_1, B_2, \ldots, B_n\}$ was a potential parent reactant of the mass spectrum peak; the substance reaction database is KEGG database and HMDB database; the network relationship diagram of the substance reaction was a topological relationship with the minimum mass difference of the substance reaction as a link, the mass spectrum peak as a node, and the correlation value≥0.8. Where, the minimum mass difference is calculated according to the following formula:

$PMD_{Bk} = \{\min(|B_k - P_1|, |B_k - P_2|, \ldots, |B_k - P_m|)\}$
$k = 1, 2, \ldots, n\};$ Step 5: Screening the substance reaction relationship of DON. According to the matching rules that the mass spectrum peak error was <3 ppm, the retention time error was <1 min, the relative molecular mass of the DON molecule containing an even number of nitrogen atoms was an even number, the relative molecular mass of the DON molecule containing an odd number of nitrogen atoms was an odd number, and the score for molecular formula matching was >90, the mass spectrum peaks in the network relationship diagram was matched with the mass spectral database to obtain the molecular formula of the substance corresponding to the mass spectrum peak, and the high-frequency mass difference relationship associated with DON in the network relationship diagram was screened, to obtain a substance reaction relationship of DON.

Step 6: Determining different sources of DON: Calculating the reaction relationship connectivity degree and a reaction distance of each DON molecule in the substance reaction relationship of DON, and dividing exogenous DON and endogenous DON according to the reaction relationship connectivity degree and the reaction distance. The connectivity degree was the number of substance reactions in which each DON molecule was involved in the adjacency matrix of the substance reaction relationship. The reaction distance was a connection distance among DON molecules in the adjacency matrix of the substance reaction relationship, that is, in the adjacency matrix $A=(a_{ij})_{N \times N}$, the connectivity degree of DON molecules was $k_i = \Sigma_{j=1}^{N} a_{ij}$, and the reaction distance of DON molecules was $$L = \frac{1}{\frac{1}{2}N(N-1)} \sum_{i \geq j} l_{ij},$$

where, A was an adjacency matrix, $a_{ij}$ was a relationship descriptor between DON molecule i and DON molecule j, N was the number of DON molecules, $k_i$ was the connectivity degree of DON molecule i, and $l_{ij}$ was the number of the shortest connection relationship between DON molecule i and DON molecule j, L was the average connection length of the substance reaction relationship network of DON. The division by the reaction relationship connectivity degree and the reaction distance was to use the median of the connectivity degree in the wastewater sample as the main cut-off value and the median of the reaction distance as the secondary cut-off value, to divide DON molecules of $\{k_i \leq \text{median}(k_i)\} \cap \{l_{ij} \geq \text{median}(l_{ij})\}$ as exogenous DON molecules, and DON molecules of $\{k_i > \text{median}(k_i)\} \cup \{l_{ij} < \text{median}(l_{ij})\}$ as endogenous DON molecules, where median($k_i$) was the median of the connectivity degree, and median($l_{ij}$) was the median of the reaction distance.

Figure 3:
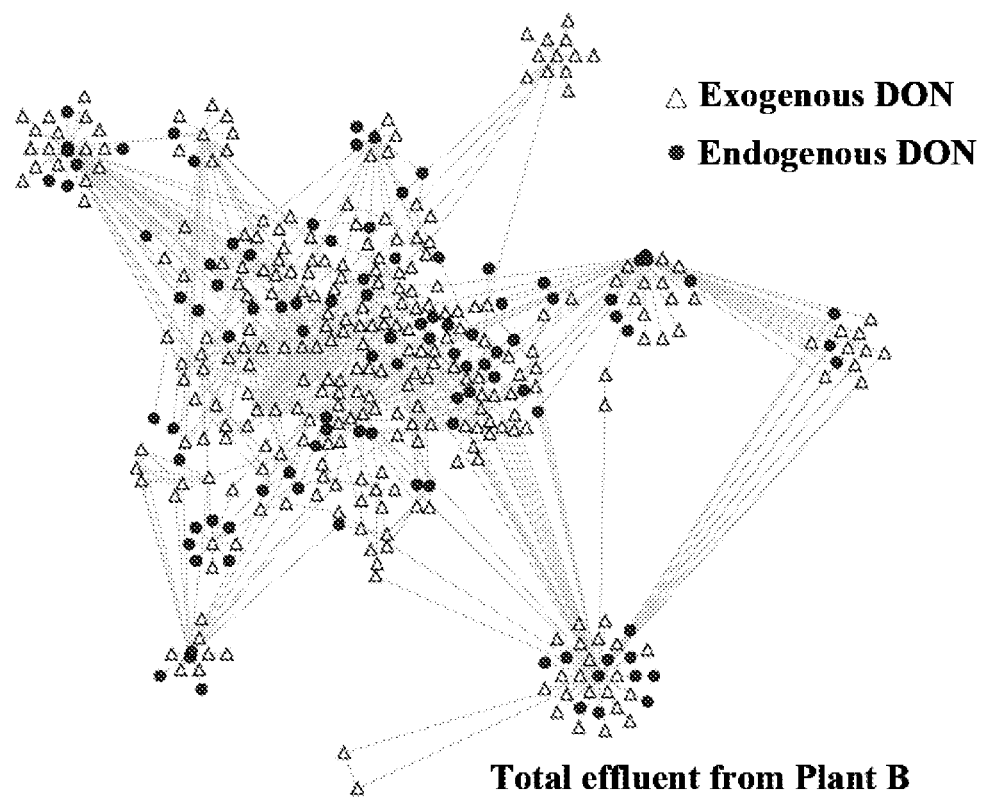
FIG. 3 is a topological structure diagram of a substance reaction of DON from different sources according to Example 2 of the disclosure.

As shown in FIG. 3, the DON molecules in the total effluent from Plant B were divided into exogenous DON molecules and endogenous DON molecules by this method, and then the mass spectrum peak intensities of exogenous DON molecules and endogenous DON molecules were calculated respectively. Thus, it could be confirmed that, in the total effluent from Plant A with a DON concentration at 3.11 mg/L, the exogenous DON accounted for 62.5%, and endogenous DON accounted for 37.5%.

Example 3

Different from Example 1, the application object of this example was an effluent of an upgrading and reconstruction section of a wastewater treatment plant C, with a daily treatment capacity of wastewater of 60,000 cubic meters per day and an oxidation ditch as the main process. After upgrading and reconstruction, a coagulation tank and a denitrification filter were added. The total effluent of the upgrading and reconstruction section contained COD 13.13 mg/L, total nitrogen 7.34 mg/L, total phosphorus 0.03 mg/L, ammonia nitrogen 0.16 mg/L, nitrate nitrogen 2.94 mg/L, nitrite nitrogen 0.06 mg/L, DON 4.18 mg/L. The steps for identifying and analyzing exogenous DON and endogenous DON in the effluent from the upgrading and reconstruction section of Plant C were shown in FIG. 1. A method for identifying and analyzing dissolved organic nitrogen of different sources in wastewater, which was a simultaneous qualitative and quantitative method for exogenous DON and endogenous DON in wastewater samples established by liquid chromatography-high resolution mass spectrometry technology and reaction omics analysis technology, comprised the following steps:

Step 1: Extracting DON in wastewater. A commercial SPE cartridges with styrene/DVB copolymer as the filler was used to concentrate and enrich DON in the wastewater sample. Wastewater samples were firstly filtered through a 0.45 cellulose acetate filter membrane, and acidified with ACS grade high-purity hydrochloric acid to pH 2, then the SPE cartridges were activated using 12 mL of LC-MS grade methanol and 20 mL of ultrapure water with pH 2. Samples were loaded at a flow rate of 1.0 mL/min, then SPE cartridges were rinsed with 25 mL of pH 2 ultrapure water, and finally dried with nitrogen. After eluted with 5 mL of LC-MS grade methanol, DON extract to be detected was obtained. Before testing on the machine, the DON extract was filtered through a 0.22 μm organic filter membrane, and the concentration of the dissolved organic carbon was 50 mg/L.

Step 2: Detecting mass spectrum peaks in the DON extract. A full scan analysis and detection of the DON extract was performed using a LC-HRMS. The scanning mode of the LC-HRMS was set to ionization mode of positive ions and negative ions, the ionization source was electrospray ionization source, the flow rate was 0.4 mL/min, the range of the collected spectra was 150-1200 Da. The detection spectrum of DON in the wastewater sample was obtained after testing on the machine;

Step 3: Pre-processing the spectral data of the wastewater samples. Using ultrapure water as a sample to be treated, the operation procedure same as those for the wastewater samples were carried out to obtain background signals; the background signals were subtracted by a peak intensity subtraction method, and the mass spectrum peaks with peak intensity≥2000 after the subtraction were retained. The background subtraction, elimination of interference peaks, and elimination of noise signals were performed for the detection spectrum of wastewater samples, and then the wastewater sample spectral data were converted into ".mzrt" data by the "XCMS" program package in the R language;

Step 4: Constructing a network relationship of the substance reaction in the wastewater: performing extraction of peaks of the spectral data of the wastewater samples, hierarchical clustering of the retention time, and peak de-redundancy of the wastewater samples using a reaction omics analysis technology, to simplify the spectral data of the wastewater samples; establishing a global reaction quality difference relationship, screening independent mass spectrum peaks, and constructing a high-frequency mass difference matrix of the substance reaction in the wastewater sample; combining the high-frequency mass difference matrix and the substance reaction database to generate a network relationship diagram of the substance reaction in the wastewater. For the reaction omics analysis technology, in the process of biochemical reaction, the substance reaction process in which the DON was involved had its corresponding reactant DON and reaction product DON, and a specific relationship between the reactant DON and the reaction product DON; under the condition that the substance reaction process was unknown, the substance reaction process involving the reactant DON, the reaction product DON, and DON in the sample could be obtained according to the mass difference relationship; The peak de-redundancy was to deduct redundant mass spectrum peaks in the spectral data of the wastewater samples; The hierarchical clustering of the retention time was to calculate the mass difference relationship in wastewater samples using the "getpaired" function in the R language, and cluster the retention time according to the recursion formula $$D = \frac{\sqrt{(RT_m - RT_j)^2} + \sqrt{(RT_n - RT_j)^2}}{2},$$

with a D value greater than 15 as the cutoff grouping threshold. Where, $RT_m$ and $RT_n$ were combined clusters of retention time data; $RT_1$ was a single retention time data to be calculated, and D was the distance between $RT_1$ and the combined clusters ($RT_m$, $RT_n$) of the retention time data; the high-frequency mass difference relationship was a mass difference relationship after deducting the adduct, neutral loss, isotope, and common fragments in the mass difference relationship using the "getstd" function in the R language; the high-frequency mass difference matrix was a substance reaction matrix with the mass spectrum peak as a matrix element, namely:

|       | $B_1$         | $B_2$         | ... | $B_n$         |
|-------|---------------|---------------|-----|---------------|
| $P_1$ | $|B_1 - P_1|$ | $|B_2 - P_1|$ | ... | $|B_n - P_1|$ |
| $P_2$ | $|B_1 - P_2|$ | $|B_2 - P_2|$ | ... | $|B_n - P_2|$ |
| ...   | ...           | ...           | ... | ...           |
| $P_m$ | $|B_1 - P_m|$ | $|B_2 - P_m|$ | ... | $|B_n - P_m|$ |

Where, $\{P_1, P_2, \ldots, P_m\}$ was a mass spectrum peak, and $\{B_1, B_2, \ldots, B_n\}$ was a potential parent reactant of the mass spectrum peak; the substance reaction database is KEGG database and HMDB database; the network relationship diagram of the substance reaction was a topological relationship with the minimum mass difference of the substance reaction as a link, the mass spectrum peak as a node, and the correlation value ≥0.7. The minimum mass difference is calculated according to the following formula:

$PMD_{Bk} = \{\min(|B_k - P_1|, |B_k - P_2|, \ldots, |B_k - P_m|)|$
$k=1, 2, \ldots, n\};$ Step 5: Screening the substance reaction relationship of DON. According to the matching rules that the mass spectrum peak error was <4 ppm, the retention time error was <1.5 min, the relative molecular mass of the DON molecule containing an even number of nitrogen atoms was an even number, the relative molecular mass of the DON molecule containing an odd number of nitrogen atoms was an odd number, and the score for molecular formula matching was >90, the mass spectrum peaks in the network relationship diagram was matched with the mass spectral database to obtain the molecular formula of the substance corresponding to the mass spectrum peak, and the high-frequency mass difference relationship associated with DON in the network relationship diagram was screened, to obtain a substance reaction relationship of DON;

Step 6: Determining different sources of DON: Calculating the reaction relationship connectivity degree and a reaction distance of each DON molecule in the substance reaction relationship of DON, and dividing exogenous DON and endogenous DON according to the reaction relationship connectivity degree and the reaction distance. The connectivity degree was the number of substance reactions in which each DON molecule was involved in the adjacency matrix of the substance reaction relationship. The reaction distance was a connection distance among DON molecules in the adjacency matrix of the substance reaction relationship, that is, in the adjacency matrix $A = (a_{ij})_{N \times N}$, the connectivity degree of DON molecules was $k_i = \sum_{j=1}^{N} a_{ij}$, and the reaction distance of DON molecules was $$L = \frac{1}{\frac{1}{2}N(N-1)} \sum_{i \geq j} l_{ij},$$

where, A was an adjacency matrix, $a_{ij}$ was a relationship descriptor between DON molecule i and DON molecule j, N was the number of DON molecules, $k_i$ was the connectivity degree of DON molecule i, and $l_{ij}$ was the number of the shortest connection relationship between DON molecule i and DON molecule j, L was the average connection length of the substance reaction relationship network of DON. The division by the reaction relationship connectivity degree and the reaction distance was to use the median of the connectivity degree in the wastewater sample as the main cut-off value and the median of the reaction distance as the secondary cut-off value, to divide DON molecules of $\{k_i \leq \text{median}(k_i)\} \cap \{l_{ij} \geq \text{median}(l_{ij})\}$ as exogenous DON molecules, and DON molecules of $\{k_i > \text{median}(k_i)\} \cup \{l_{ij} < \text{median}(l_{ij})\}$ as endogenous DON molecules, where median($k_i$) was the median of the connectivity degree, and median($l_{ij}$) was the median of the reaction distance.

Figure 4:
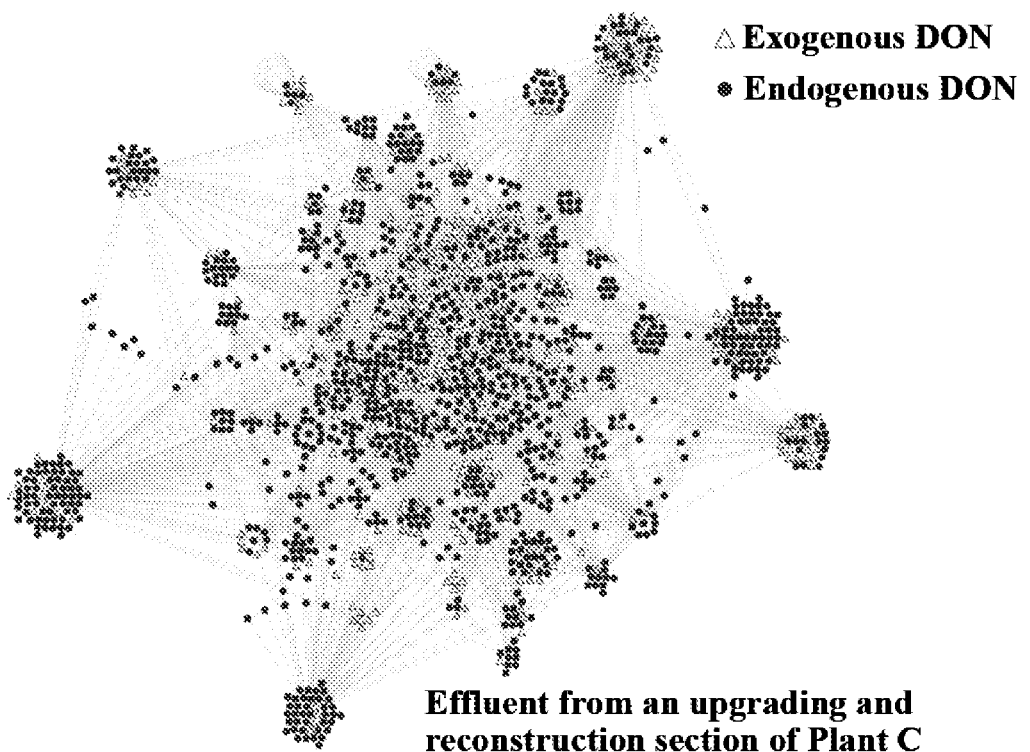
FIG. 4 is a topological structure diagram of a substance reaction of DON from different sources according to Example 3 of the disclosure.

As shown in FIG. 4, the DON molecules in the effluent from the upgrading and reconstruction section of Plant C were divided into exogenous DON molecules and endogenous DON molecules by this method, and then the mass spectrum peak intensities of exogenous DON molecules and endogenous DON molecules were calculated respectively. Thus, it could be confirmed that, in the effluent from the upgrading and reconstruction section of Plant C with a DON concentration at 4.18 mg/L, the exogenous DON accounted for 28.6%, and endogenous DON accounted for 71.4%.

It will be obvious to those skilled in the art that changes and modifications may be made, and therefore, the aim in the appended claims is to cover all such changes and modifications.

What is claimed is:
1. A method for identifying and analyzing dissolved organic nitrogen of different sources in wastewater, the method comprising:
   a) separating dissolved organic nitrogen (DON) from interferents of a wastewater sample through operations comprising pretreatment of the wastewater sample, column activation, sample loading, leaching, and elution using solid phase extraction cartridges (SPE cartridges), concentrating and enriching DON in the wastewater sample, to obtain a DON extract;
   b) performing full scan analysis and detection of the DON extract using a liquid chromatography-high resolution mass spectrometer (LC-HRMS), to obtain a detection spectrum of DON in the wastewater sample;
   c) performing subtraction of background signal values, elimination of interference peaks, and elimination of noise signals from the detection spectrum of DON in the wastewater sample, to obtain preprocessed spectral data of the wastewater sample;
   d) performing extraction of peaks of the spectral data of the wastewater sample, hierarchical clustering of a retention time of peaks of the spectral data, and peak de-redundancy of the wastewater sample using a reac- tion omics analysis technology, to simplify the spectral data of the wastewater sample;

establishing a global reaction quality difference relationship, screening independent mass spectrum peaks, and constructing a high-frequency mass difference matrix of a substance reaction in the wastewater sample; combining the high-frequency mass difference matrix and a substance reaction database to generate a network relationship diagram of the substance reaction in the wastewater sample;

e) matching the mass spectrum peaks in the network relationship diagram with a mass spectral database to obtain a molecular formula of the substance corresponding to the mass spectrum peaks, screening a high-frequency mass difference relationship associated with DON in the network relationship diagram to obtain a substance reaction relationship of DON; and f) calculating a reaction relationship connectivity degree and a reaction distance of each DON molecule in the substance reaction relationship of DON, and dividing exogenous DON and endogenous DON according to the reaction relationship connectivity degree and the reaction distance.

2. The method of claim 1, wherein the wastewater sample is selected from a single treatment unit in an urban wastewater treatment plant, a collection of wastewater samples from a plurality of treatment units in an urban wastewater treatment plant, a collection of wastewater samples from an entire process of an urban wastewater treatment plant, and effluent samples from an urban wastewater treatment plant; exogenous DON is the DON that has not been completely degraded in a wastewater treatment process, and the DON that is non-degradable or difficult to biodegrade in an influent; endogenous DON is a microbial DON, a microbial conversion product of exogenous DON, and a DON by-product of the wastewater treatment process.

3. The method of claim 1, wherein in a), the SPE cartridges are commercial SPE cartridges using styrene-divinylbenzene copolymer as a filler; the pretreatment of the wastewater sample is to filter the wastewater sample through a 0.45 μm cellulose acetate filter membrane and acidify the wastewater sample to pH 2 using an ACS grade high-purity hydrochloric acid; the column activation is to pass 10-15 mL of LC-MS grade methanol and 20-25 mL of ultrapure water with pH 2 through the SPE cartridges; the leaching is to pass 20-25 mL of ultrapure water with pH 2 through the SPE cartridges; the elution is to blow the SPE cartridges with nitrogen to remove a liquid therein and then pass 5-15 mL of LC-MS grade methanol through the SPE cartridges; a flow rate of an eluent passing through the SPE cartridges is controlled to be 0.5-2.0 mL/min; the DON extract is filtered through a 0.22 μm organic filter membrane before being tested on a machine, and a concentration of dissolved organ carbon of the DON extract is 50-100 mg/L.

4. The method of claim 1, wherein in b), the LC-HRMS operates under the following parameters: a scanning mode is a positive ion and negative ion mode; an ionization source is electrospray ionization source, and a flow rate is 0.2-0.5 mL/min; and a range of a collected spectra is 50-1200 Da.

5. The method of claim 1, wherein in c), the background signal values are acquired as follows: background signals are acquired through operations in a) and b) using ultrapure water as a sample to be processed; the background signals are subtracted by a peak intensity subtraction method, and the mass spectrum peaks with a peak intensity ≥1000 after subtraction are retained; and the spectral data of the wastewater sample are ".mzrt" data converted by a "XCMS" program package in a R language.

6. The method of claim 1, wherein:

in d), for the reaction omics analysis technology, in the process of biochemical reaction, DON involved in a substance reaction process comprises corresponding reactant DON and reaction product DON, and a mass difference relationship exists between the reactant DON and the reaction product DON; in unknown conditions, the substance reaction process of the reactant DON, the reaction product DON, and DON in the wastewater sample is obtained according to the mass difference relationship;

the peak de-redundancy is to deduct redundant mass spectrum peaks in the spectral data of the wastewater sample;

the hierarchical clustering of the retention time is to calculate the mass difference relationship in the wastewater sample using the "getpaired" function in the R language, and cluster the retention time according to a recursion formula (1), with a D value greater than 10 as a cutoff grouping threshold:

$$D = \frac{\sqrt{(RT_m - RT_j)^2} + \sqrt{(RT_n - RT_j)^2}}{2}; \quad (1)$$

where, $RT_m$ and $RT_n$ are combined clusters of retention time data; $RT_1$ is a single retention time data to be calculated, and D is a distance between $RT_1$ and a combined clusters ($RT_m$, $RT_n$) of the retention time data;

the high-frequency mass difference relationship is a mass difference relationship after deducting an adduct, neutral loss, isotope, and common fragments in the mass difference relationship using the "getstd" function in the R language; the high-frequency mass difference matrix is a substance reaction matrix with the mass spectrum peaks as a matrix element according to the formula (2):

$$\begin{array}{c|cccc} & B_1 & B_2 & \ldots & B_n \\ P_1 & |B_1 - P_1| & |B_2 - P_1| & \ldots & |B_n - P_1| \\ P_2 & |B_1 - P_2| & |B_2 - P_2| & \ldots & |B_n - P_2| \\ \ldots & \ldots & \ldots & \ldots & \ldots \\ P_m & |B_1 - P_m| & |B_2 - P_m| & \ldots & |B_n - P_m| \end{array} \quad (2)$$

where, $\{P_1, P_2, \ldots, P_m\}$ is the mass spectrum peaks, and $\{B_1, B_2, \ldots, B_n\}$ is a potential parent reactant of the mass spectrum peaks;

the substance reaction database is KEGG database and HMDB database; and the network relationship diagram of the substance reaction is a topological relationship with a minimum mass difference of the substance reaction as a link, the mass spectrum peaks as a node, and a correlation value ≥0.6.

7. The method of claim 6, wherein the minimum mass difference is calculated according to the following formula:

$$PMD_{Bk} = \{\min(|B_k - P_1|, |B_k - P_2|, \ldots, |B_k - P_m|)|$$
$$k = 1, 2, \ldots, n\} \quad (3);$$

where, $PMD_{BK}$ is the minimum mass difference of the substance reaction, $\{P_1, P_2, \ldots, P_m\}$ is the mass spectrum peaks, and $\{B_1, B_2, \ldots, B_n\}$ is a potential parent reactant of the mass spectrum peaks.

8. The method of claim 1, wherein in e), a molecular formula matching rule of the substance corresponding to the mass spectrum peaks is that a mass spectrum peak error is <5 ppm, a retention time error is <2 min, a relative molecular mass of the DON molecule containing an even number of nitrogen atoms is an even number, a relative molecular mass of the DON molecule containing an odd number of nitrogen atoms is an odd number, and a score for molecular formula matching is >90.

9. The method of claim 1, wherein:

in f), the reaction relationship connectivity degree is a number of substance reactions in which each DON molecule is involved in an adjacency matrix of the substance reaction relationship;

the reaction distance is a connection distance among DON molecules in the adjacency matrix of the substance reaction relationship; in the adjacency matrix $A=(a_{ij})_{N\times N}$, the connectivity degree of DON molecules is $k_i=\Sigma_{j=1}^{N} a_{ij}$, and the reaction distance of DON molecules is $$L = \frac{1}{\frac{1}{2}N(N-1)} \sum_{i \geq j} l_{ij},$$

where, A is an adjacency matrix, $a_{ij}$ is a relationship descriptor between DON molecule i and DON molecule j, N is a number of DON molecules, $k_i$ is a connectivity degree of DON molecule i, and $l_{ij}$ is a number of a shortest connection relationship between DON molecule i and DON molecule j, L is an average connection length of the substance reaction relationship network of DON; and the division by the reaction relationship connectivity degree and the reaction distance is to use a median of the connectivity degree in the wastewater sample as a main cut-off value and a median of the reaction distance as a secondary cut-off value, to divide DON molecules of $\{k_i \leq \mathrm{median}(k_i)\} \cap \{l_{ij} \geq \mathrm{median}(l_{ij})\}$ as exogenous DON molecules, and DON molecules of $\{k_i > \mathrm{median}(k_i)\} \cup \{l_{ij} < \mathrm{median}(l_{ij})\}$ as endogenous DON molecules, $\mathrm{median}(k_i)$ is the median of the connectivity degree, and $\mathrm{median}(l_{ij})$ is the median of the reaction distance.

10. A method for qualitative and quantitative determination of exogenous and endogenous dissolved organic nitrogen in wastewater, the method comprising applying the method of claim 1.

* * * * *